United States Patent [19]

Hirano et al.

[11] Patent Number: 5,338,356

[45] Date of Patent: * Aug. 16, 1994

[54] CALCIUM PHOSPHATE GRANULAR CEMENT AND METHOD FOR PRODUCING SAME

[75] Inventors: Masahiro Hirano, Saitama; Hiroyasu Takeuchi, Hanno, both of Japan

[73] Assignee: Mitsubishi Materials Corporation, Tokyo, Japan

[*] Notice: The portion of the term of this patent subsequent to Oct. 6, 2009 has been disclaimed.

[21] Appl. No.: 964,203

[22] Filed: Oct. 21, 1992

[30] Foreign Application Priority Data

Oct. 29, 1991 [JP] Japan ................... 3-283212
Oct. 29, 1991 [JP] Japan ................... 3-283213
Oct. 29, 1991 [JP] Japan ................... 3-283214

[51] Int. Cl.$^5$ ............................................. C04B 12/02
[52] U.S. Cl. ....................................... 106/690; 106/35; 106/691

[58] Field of Search ..................... 106/35, 690, 691; 264/333, DIG. 43; C04B 12/02

[56] References Cited

U.S. PATENT DOCUMENTS

| | | | |
|---|---|---|---|
| 4,518,430 | 5/1998 | Brown et al. | 106/35 |
| 5,017,518 | 5/1991 | Hirayama et al. | 106/35 |
| 5,149,368 | 9/1992 | Liu et al. | 106/35 |
| 5,152,836 | 10/1992 | Hirano et al. | 106/35 |
| 5,180,426 | 1/1983 | Sumita | 106/35 |

*Primary Examiner*—Mark L. Bell
*Assistant Examiner*—Paul Marcantoni
*Attorney, Agent, or Firm*—Malcolm B. Wittenberg

[57] ABSTRACT

A calcium phosphate granular cement contains mixed powders obtained by mixing α-type calcium tertiary phosphate or calcium quaternary phosphate with a calcium phosphate compound selected from calcium primary phosphate, calcium secondary phosphate and mixtures thereof at a Ca/P molar ratio of 1.35 to 1.49 or 1.30 to 1.90. A minimum diameter of each cement granule is 0.1 to 1.0 mm.

9 Claims, No Drawings

CALCIUM PHOSPHATE GRANULAR CEMENT AND METHOD FOR PRODUCING SAME

BACKGROUND OF THE INVENTION

This invention relates to a calcium phosphate granular cement to be charged into defect, hollow or absorbed portions of bone or voids left after tooth extraction, and a method for producing such cement.

Hydroxyapatite having the minimum size or diameter of 0.1 to 3.0 mm and a specific surface shape factor $\Phi$ of 6.3 to 15, as a filler to be charged into defect, hollow or absorbed portions of bone or voids left after tooth extraction, is known from, for example, Japanese Laid-Open Patent Publication No. 61-20558 (1986). Hydroxyapatite used for such portions or voids of bone is known to have superior biological affinity. As the filler for defect or hollow portions of bone of indefinite shape, granular hydroxyapatite having the above-mentioned minimum size and the specific surface shape factor has proven to be the most adequate.

However, the granular hydroxyapatite cannot retain its shape satisfactorily even after compaction such that before a bone tissue is formed in the vicinity of the site of incision after lapse of two to three weeks after surgical operation, the charged product tends to leak out of the site of incision to retard the recovery of the charged site. It is, therefore, crucial to maintain the mass of charged compacted hydroxyapatite granules in its initial shape for promoting the therapy.

For overcoming this drawback, there has been proposed in, for example Japanese Laid-Open Patent Publications Nos. 3-45266 (1991) and 3-51051 (1991) a calcium phosphate cement in which a hydraulic calcium phosphate cement and hydroxyapatite granules are combined for fixing the hydroxyapatite granules with hydraulic calcium phosphate cement. However, although the calcium phosphate cement is able to fix the hydroxyapatite granules, fine powders of the hydraulic calcium phosphate cement is intruded and embedded in gaps defined between hydroxyapatite granules to stop the pores leading from the surface into the inside of the charged mass so that the living tissue or blood vessels cannot be introduced through the charged site to obstruct the transport of nutrients or growth of now bone.

SUMMARY OF THE INVENTION

It is an object of the present invention to provide a calcium phosphate granular cement which can be charged easily into defect, hollow or absorbed portions of bone of any arbitrary size or voids left after tooth extraction without stimulating the living tissue, which can be turned promptly in vivo into apatite and which has voids between cement granules in the charged mass which are useful for transporting the nutrient and for formation of new bone, and a method for producing the calcium phosphate granular cement.

It is another object of the present invention to provide a calcium phosphate granular cement which may be hardened immediately after charging same into the living body without fear of leakage and which has excellent shape retention characteristics at an initial stage after the end of surgical operation.

The above and other objects of the present invention will become apparent from the following description.

In accordance with the present invention, there is provided a calcium phosphate granular cement comprising mixed powders obtained by mixing $\alpha$-type calcium tertiary phosphate with a calcium phosphate compound selected from calcium primary phosphate, calcium secondary phosphate and mixtures thereof at a Ca/P molar ratio of 1.35 to 1.49, the minimum diameter of each cement granule being 0.1 to 1.0 mm. This cement is referred to hereinafter as the first calcium phosphate granular cement.

In accordance with the present invention, there is also provided a method for producing a calcium phosphate granular cement comprising mixing $\alpha$-type calcium tertiary phosphate with a calcium phosphate compound selected from calcium primary phosphate, calcium secondary phosphate and mixtures thereof at a Ca/P molar ratio of 1.35 to 1.49, pressing the resulting powder mixture, and again dividing the pressed product into granules each having a minimum diameter of 0.1 to 1.0 mm. This method is referred to hereinafter as the first method for producing the calcium phosphate granular cement.

In accordance with the present invention, there is also provided a calcium phosphate granular cement comprising mixed powders obtained by mixing calcium quaternary phosphate with a calcium phosphate compound selected from calcium primary phosphate, calcium secondary phosphate and mixtures thereof at a Ca/P molar ratio of 1.30 to 1.90, the minimum diameter of each cement granule being 0.1 to 1.0 mm. This granular cement is referred to hereinafter as the second calcium phosphate granular cement.

Finally, there is provided a method for producing a calcium phosphate granular cement comprising mixing calcium quaternary phosphate with a calcium phosphate compound selected from calcium primary phosphate, calcium secondary phosphate and mixtures thereof at a Ca/P molar ratio of 1.30 to 1.90, pressing the resulting powder mixture and again dividing the pressed product into granules each having a minimum diameter of 0.1 to 1.0 mm. This method is referred to hereinafter as the second method for producing the calcium phosphate granular cement.

PREFERRED EMBODIMENTS OF THE INVENTION

The present invention will be explained in detail hereinbelow.

The powders used as a main component of the first calcium phosphate granular cement according to the present invention are mixed powders composed of $\alpha$-type calcium tertiary phosphate, calcium primary phosphate and/or calcium secondary phosphate.

Turning more concretely to the reaction of these components, the $\alpha$-type calcium tertiary phosphate and calcium primary phosphate are components reacted in the presence of water to yield calcium secondary phosphate and octacalcium phosphate so as to be hardened, while calcium secondary phosphate and octacalcium phosphate are components promptly turned in vivo into hydroxyapatite. On the other hand, $\alpha$-type calcium tertiary phosphate and calcium secondary phosphate, when mixed together in the presence of water, are reacted together to yield octacalcium phosphate so as to be hardened by entanglement of octacalcium phosphate crystals, while octacalcium phosphate is a component gradually turned in vivo into apatite. As $\alpha$-type calcium tertiary phosphate, $\alpha$-type calcium tertiary phosphate produced by wet synthesis using an aqueous solution of phosphoric acid and calcium hydroxide, or $\alpha$-type calcium tertiary phosphate produced by dry synthesis of powders of secondary calcium phosphate and powders of calcium carbonate, may preferably be employed. As calcium primary phosphate, calcium primary phosphate monohydrate, which is commercially available, is preferred. As calcium secondary phosphate, calcium secondary phosphate dihydrate or anhydride, which is similarly commercially available, is preferred.

α-Type calcium tertiary phosphate, calcium primary phosphate and/or calcium secondary phosphate are mixed in such proportions that the Ca/P molar ratio is in the range of from 1.35 to 1.49. If the molar ratio is less than 1.35, the hardened product is lowered in strength, whereas if the molar ratio exceeds 1.49, the cement granules, while being hardened, are not bonded together so that the resulting product, when charged into a living body, is unable to form a block-shaped unitary hardened mass. If a mixture of calcium primary phosphate and calcium secondary phosphate is employed, the mixing ratio of calcium secondary phosphate may preferably be not more than 10 wt % and, above all, not more than 5 wt %, based on the total weight of the powders. If the mixing ratio exceeds 10 wt %, the strength of the produced hardened mass is undesirably lowered.

On the other hand, powders employed as main components of the second calcium phosphate granular cement of the present invention are powder mixtures composed of calcium quaternary phosphate, calcium primary phosphate and/or calcium secondary phosphate.

Turning more concretely to the reaction of these components, calcium quaternary phosphate and calcium primary phosphate are components which, when mixed in the presence of water, are reacted together to yield crystals of calcium secondary phosphate and octacalcium phosphate which are entangled together so as to be hardened, whereas calcium quaternary phosphate and calcium secondary phosphate are components, which when mixed together in the presence of water, are reacted together to yield crystals of octacalcium phosphate which are entangled together so as to be hardened. On the other hand, calcium secondary phosphate and octacalcium phosphate are components which are gradually turned in vivo into apatite.

As calcium quaternary phosphate, calcium quaternary phosphate yielded by dry synthesis, using calcium secondary phosphate and calcium carbonate, or calcium quaternary phosphate yielded by wet synthesis, using calcium hydroxide and phosphoric acid, may preferably be employed, whereas calcium primary phosphate or calcium secondary phosphate may be exemplified by the compounds similar to those enumerated in connection with the first calcium phosphate granular cement.

The mixing ratio of calcium quaternary phosphate and calcium primary phosphate and/or calcium secondary phosphate is so selected that the Ca/P molar ratio is in a range of from 1.30 to 1.90. The mixing ratio outside the above range is not desirable because it takes much time to be hardened and the hardened mass has only low mechanical strength.

Although there is no limitation to the mixing ratio of calcium primary phosphate and calcium secondary phosphate, the hardening time is shortened if calcium primary phosphate is used in an excessive amount, whereas the mechanical strength is increased if calcium secondary phosphate is used in an excessive amount.

The first and second calcium phosphate granular cements of the present invention need to be 0.1 to 1.0 mm in size or diameter of the cement granule at the minimum. If the minimum diameter is less than 0.1 mm, there is no sufficient void left between the granules, whereas if it exceeds 1.0 mm, the cement granules are contacted with one another with an area which is excessively small so that the granules are not bonded together and consequently the charged product in its entirety is unable to form a block-shaped hardened mass. By more finely controlling the granule size, it becomes possible to control the size of the void between the granules or the strength of the charged product in its entirety. For example, if the granular cement classified to a granule size of 0.1 to 0.3 mm is hardened, the voids between the granules are reduced in size with the charged product in its entirety being increased in strength. On the other hand, the granular cement classified to have the granule size of 0.7 to 1.0 mm has a larger size of the voids, although it is not so high in mechanical strength, but a larger tissue, such as blood vessel may be led through the voids.

The first and second calcium phosphate granular cements of the present invention may be sufficiently hardened with water components contained in the body fluid so that satisfactory results may be achieved with the above powders alone. However, these cements may also be mixed with water or sterilized physiological saline, if so desired. Besides, sodium succinate, sodium lactate, etc. may also be dissolved in the above water components for further reducing the hardening time. The quantity of the water components may desirably be 300 to 30 parts by weight to 100 parts by weight of the powders.

According to the first method for preparing the first calcium phosphate granular cement of the present invention, powders of α-type calcium tertiary phosphate are mixed with powders of calcium primary phosphate and/or powders of calcium secondary phosphate at a Ca/P molar ratio of 1.35 to 1.49 to give a powder mixture, which is pressed and again divided to form granules having a minimum diameter of 0.1 to 1.0 mm.

According to the second method for preparing the second calcium phosphate granular cement of the present invention, powders of calcium quaternary phosphate are mixed with powders of calcium primary phosphate and/or powders of calcium secondary phosphate at a Ca/P molar ratio of 1.30 to 1.90 to give a powder mixture, which is pressed and again divided to form granules having a minimum diameter of 0.1 to 1.0 mm.

It is preferred that the powders used in the first and second methods of the present invention be separately divided by an automatic mortar, a ball mill or a jet mill or by spray-drying and screened through a sieve having a mesh size of 88 μm.

For achieving mixing at the above-mentioned particular Ca/P molar ratio, an automatic mortar, a ball mill or a shaker mixer may be employed.

In the first and second methods of the present invention, the pressing operation may be performed by a hydraulic hand press or a hydrostatic press. The pressure used for the pressing operation may preferably be not less than 200 kgf/cm$^2$. The pressure less than 200 kgf/cm$^2$ is not desirable because the strength of the individual granules is lowered so that the granules tend to be destroyed easily during the handling stage prior to hardening to produce fine powders, which may be intruded and embedded in the interstices between the cement granules. Although there is no limitation to the upper limit of the pressure, it may preferably be not more than 2000 kgf/cm$^2$ in view of the capacity of the customary hydrostatic press and pulverizability of the compressed powders.

For re-dividing the pressed molded body produced by pressing in the first and second methods of the present invention, an automatic mortar or a ball mill may preferably be employed. The produced powders may be screened through a sieve to have a minimum granule size of 0.1 to 1.0 mm to produce the desired first or second calcium phosphate granular cement.

Besides, according to the first and second methods of the present invention, the produced powders are mixed together and pressed and the pressed mass is again divided to form granules to afford sufficient strength to the individual granules as well as to produce a porous mass on hardening and bonding of the granules to one another.

The first and second calcium phosphate granular cements of the present invention may be charged easily into defect, hollow or absorbed portions of bone or cavities left after tooth extraction and may be turned promptly into apatite after being hardened. Besides, the charged mass in its entirety may be hardened into a block having voids or pores in a manner convenient for transport of nutrients or formation of new bone. The cements of the present invention are superior in initial shape retention characteristics while being substantially free from the risk of leakage from the charged site. The time necessary for therapy may also be diminished. In addition, according to the first and second methods according to the present invention, the above-described first and second calcium phosphate granular cements may be produced easily.

EXAMPLES OF THE INVENTION

Preparation Examples 1-1 to 1-7

$\alpha$-Type calcium tertiary phosphate was pulverized using an automatic mortar, while calcium secondary phosphate dihydrate produced by WAKO PURE CHEMICAL INDUSTRIES, LTD. extra class, was pulverized using a ball mill. The resulting powders of $\alpha$-type calcium tertiary phosphate and calcium secondary phosphate were screened through a sieve having a mesh size of 88 $\mu$m and adjusted so that the Ca/P molar ratio was equal to 1.45. The resulting powders were uniformly mixed for 30 minutes by a shaker mixer, manufactured by SINMAL ENTERPRISES under the trade name of "TYPE T2C".

120 g of the resulting mixture were charged into a rectangular metal mold having a cross-sectional shape of 50×100 mm and primarily molded under a pressure of 200 kgf/cm$^2$ using a hydraulic press manufactured by RIKEN KK under a trade name of "TYPE P-18". The resulting product was pressed by a hydraulic press manufactured by RIKEN KK under special order to produce a pressed molded product.

The pressed molded product was divided by an automatic mortar manufactured by ISHIKAWA KOGYO KK under a trade name of "TYPE 20" to give powders, which were screened through sieves having mesh sizes of 0.044, 0.1, 0.3, 0.5, 0.7, 1.0 and 3.0 mm to produce seven different cement powders having particle sizes in the ranges of from 0.1 to 0.3 mm (Preparation Example 1-1), 0.3 to 0.5 mm (Preparation Example 1-2), 0.5 to 0.7 mm (Preparation Example 1-3), 0.7 to 1.0 mm (Preparation Example 1-4), 0.1 to 1.0 mm (Preparation Example 1-5), 0.044 to 1.0 mm (Preparation Example 1-6) and 1.0 to 3.0 mm (Preparation Example 1-7).

Example 1-1

5 g each of the cement powders produced in Preparation Example 1-1 to 1-5 and 5 ml of physiological saline were mixed together to produce the first calcium phosphate granular cements of the present invention. Each of the produced calcium phosphate granular cements was charged into a cylindrical mold frame having a diameter of 20 mm and maintained in a drier at 37° C. for three hours.

After drying, hardened products were taken out of the mold frames. It was found that the hardened products were in the form of porous blocks having voids between the granules.

The block-shaped products obtained by hardening the granules of the Preparation Examples 1-1 and 1-2 had compressive strengths of 25.2 kgf/cm$^2$ (Preparation Example 1-1) and 20.2 kgf/cm$^2$ (Preparation Example 1-2). For measuring the compressive strength, an Instron universal tester available under a trade name of "TYPE 1125" was employed at a crosshead rate of 0.5 mm/min.

Comparative Example 1-1

A hardening process was carried out in the same way as in Example 1-1, except that cement powders produced in Preparation Examples 1-6 and 1-7 were employed, to produce hardened cement products.

It was found that the hardened mass produced using the powders obtained in Preparation Example 1-6 had no voids between the granules, whereas the product produced using the powders obtained in Preparation Example 1-7 was not hardened and crumbled to pieces when taken out of the cylindrical mold frame so that it could not be charged in place.

Example 1-2

Powders were produced in the same manner as in Preparation Examples 1-1 to 1-7 except that the mixing ratio of $\alpha$-type calcium tertiary phosphate and calcium secondary phosphate was adjusted so that the Ca/P molar ratio was 1.35 and 1.49. The resulting powders were classified using sieves having mesh sizes of 0.3 mm and 0.7 mm to produce cement granules having the granule size of 0.3 to 0.7 mm.

These cement powders were prepared into calcium phosphate granular cements in the same way as in Example 1-1 and hardened. It was found that the hardened products were in the form of porous blocks.

Preparation Examples 2-1 to 2-7

$\alpha$-Type calcium tertiary phosphate was pulverized using an automatic mortar, while calcium primary phosphate monohydrate produced by WAKO PURE CHEMICAL INDUSTRIES, LTD. for use as food additives, was pulverized using a ball mill. The resulting powders of $\alpha$-type calcium tertiary phosphate and calcium primary phosphate were screened through a sieve having a mesh size of 88 $\mu$m and adjusted so that the Ca/P molar ratio was equal to 1.45. The resulting powders were mixed uniformly by a shaker mixer manufactured by SINMAL ENTERPRISES under the trade name of "TYPE T2C" for 30 minutes.

120 g of the resulting mixture was charged into a rectangular metal mold having a cross-sectional shape of 50×100 mm and primarily molded under a pressure of 200 kgf/cm$^2$ using a hydraulic press manufactured by RIKEN KK under a trade name of "TYPE P-18". The resulting product was pressed by a hydraulic press manufactured by RIKEN KK under special order to produce a pressed molded product.

The pressed molded product was pulverized by an automatic mortar manufactured by ISHIKAWA KOGYO KK under a trade name of "TYPE 20" to give powders, which were then screened through sieves having mesh sizes of 0.044, 0.1, 0.3, 0.5, 0.7, 1.0 and 3.0 mm to produce seven different cement powders having particle sizes in the ranges of from 0.1 to 0.3 mm (Preparation Example 2-1), 0.3 to 0.5 mm (Preparation Example 2-2), 0.5 to 0.7 mm (Preparation Example 2-3), 0.7 to 1.0 mm (Preparation Example 2-4), 0.1 to 1.0 mm (Preparation Example 2-5), 0.044 to 1.0 mm (Preparation Example 2-6) and 1.0 to 3.0 mm (Preparation Example 2-7).

Example 2-1

5 g each of the cement powders produced in Preparation Examples 2-1 to 2-5 and 5 ml of physiological saline were mixed together to produce the first calcium phosphate granular cements of the present invention. Each of the produced calcium phosphate granular cements was charged into a cylindrical mold frame having a diameter of 20 mm and was maintained in a drier at 37° C. for three hours.

After drying, hardened products were taken out of the mold frames. It was found that the hardened products were in the form of porous blocks having voids between the granules.

The block-shaped products obtained by hardening the granules of the Preparation Examples 2-1 and 2-2 had compressive strengths of 20.7 kgf/cm$^2$ (Preparation Example 2-1) and 14.5 kgf/cm$^2$ (Preparation Example 2-2). For measuring the compressive strength, an Instron universal tester available under a trade name of "TYPE 1125" was employed at a crosshead rate of 0.5 mm/min.

Comparative Example 2-1

A hardening process was carried out in the same way as in Example 2-1, except that cement powders produced in Preparation Examples 2-6 and 2-7 were employed, to produce hardened cement products.

It was found that the hardened mass produced using the powders obtained in Preparation Example 2-6 had no voids between the granules, whereas the product produced using the powders obtained in Preparation Example 2-7 was not hardened and was crumbled to pieces when taken out of the cylindrical mold frame so that it could not be charged in place.

Example 2-2

Powders were produced in the same manner as in Preparation Examples 2-1 to 2-7 except that the mixing ratio of α-type calcium tertiary phosphate and calcium primary phosphate was adjusted so that the Ca/P molar ratio was 1.35 and 1.49. The resulting powders were classified using sieves having mesh sizes of 0.3 mm and 0.7 mm to produce cement granules having the granule size of 0.3 to 0.7 mm.

These cement powders were prepared into calcium phosphate granular cements in the same way as in Example 2-1 and hardened. It was found that the hardened products were in the form of porous blocks.

Example 2-3

Powders were produced in the same way as in Preparation Examples 2-1 to 2-7 except that calcium secondary phosphate dihydrate manufactured by WAKO PURE CHEMICAL INDUSTRIES, LTD. , extra grade, was added to a mixture of α-type calcium tertiary phosphate and calcium primary phosphate prepared in Preparation Examples 2-1 to 2-7 in an amount of 3 wt % based on the weight of the whole powders. The powders were screened through sieves having mesh sizes of 0.1, 0.3, 0.5, 0.7 and 1.0 mm to produce cement powders having particle sizes of 0.1 to 0.3 mm (powders 1), 0.3 to 0.5 mm (powders 2), 0.5 to 0.7 mm and 0.7 to 1.0 mm.

Following Example 2-1, these cement powders were prepared into calcium phosphate granular cements, which were then hardened. The resulting products were in the form of porous blocks having voids between granules.

The strengths of the hardened products produced using cement powders 1 and 2 were measured in the same way as in Example 2-1, and were found to be 23.4 kgf/cm$^2$ for powders 1 and 18.0 kgf/cm$^2$ for powders 2.

Preparation Examples 3-1 to 3-7

Calcium quaternary phosphate was pulverized using an automatic mortar, while calcium primary phosphate monohydrate produced by WAKO PURE CHEMICAL INDUSTRIES, LTD. for use as food additives, was pulverized using a ball mill. The resulting powders of calcium quaternary phosphate and calcium primary phosphate were screened through a sieve having a mesh size of 88 μm and were adjusted so that the Ca/P molar ratio was equal to 1.80. The resulting powders were uniformly mixed for 30 minutes by a shaker mixer manufactured by SINMAL ENTERPRISES under the trade name of "TYPE T2C".

120 g of the resulting mixture was charged into a rectangular metal mold having a cross-sectional shape of 50×100 mm and primarily molded under a pressure of 200 kgf/cm$^2$ using a hydraulic press manufactured by RIKEN KK under a trade name of "TYPE P-18". The resulting product was pressed by a hydraulic press manufactured by RIKEN KK under special order under a pressure of 200 kgf/cm$^2$ to produce a pressed molded product.

The pressed molded product was pulverized by an automatic mortar manufactured by ISHIKAWA KOGYO KK under a trade name of "TYPE 20 Type" to give powders, which were then screened through sieves having mesh sizes of 0.044, 0.1, 0.3, 0.5, 0.7, 1.0 and 3.0 mm to produce seven different cement powders having particle sizes in the ranges of from 0.1 to 0.3 mm (Preparation Example 3-1), 0.3 to 0.5 mm (Preparation Example 3-2), 0.5 to 0.7 mm (Preparation Example 3-3), 0.7 to 1.0 mm (Preparation Example 3-4), 0.1 to 1.0 mm (Preparation Example 3-5), 0.044 to 1.0 mm (Preparation Example 3-6) and 1.0 to 3.0 mm (Preparation Example 3-7).

Example 3-1

5 g each of the cement powders produced in Preparation Example 3-1 to 3-5 and 5 ml of physiological saline were mixed together to produce the second calcium phosphate granular cement of the present invention. Each of the produced calcium phosphate granular cement was charged into a cylindrical mold frame having a diameter of 20 mm and maintained in a drier at 37° C. for three hours.

After drying, hardened products were taken out of the mold frames. It was found that the hardened products were in the form of porous blocks having voids between the granules.

The block-shaped products obtained by hardening the granules of the Preparation Examples 3-1 and 3-2 had compressive strengths of 19.7 kgf/cm$^2$ (Preparation Example 3-1) and 13.8 kgf/cm$^2$ (Preparation Example 3-2). For measuring the compressive strength, an Instron universal tester available under a trade name of "TYPE 1125" was employed at a crosshead rate of 0.5 mm/min.

Comparative Example 3-1

A hardening process was carried out in the same way as in Example 3-1, except that cement powders produced in Preparation Examples 3-6 and 3-7 were employed, to produce hardened cement products.

It was found that the hardened mass produced using the powders obtained in Preparation Example 3-6 had no voids between the granules, whereas the product produced using the powders obtained in Preparation Example 3-7 was not hardened and was crumbled to pieces when taken out of the cylindrical mold frame so that it could not be charged in place.

Example 3-2

Powders were produced in the same manner as in Preparation Examples 3-1 to 3-7 except that the mixing ratio of calcium quaternary phosphate and calcium primary phosphate was adjusted so that the Ca/P molar ratio was 1.30 and 1.90. The resulting powders were classified using sieves having mesh sizes of 0.3 mm and 0.7 mm to produce cement granules having the granule size of 0.3 to 0.7 mm.

These cement powders were prepared into calcium phosphate granular cements in the same way as in Example 3-1 and hardened. It was found that the hardened products were in the form of porous blocks.

Example 3-3

Powders were produced in the same way as in Preparation Examples 3-1 to 3-7 except that calcium secondary phosphate dihydrate manufactured by WAKO PURE CHEMICAL INDUSTRIES LTD., extra grade, was used in place of calcium primary phosphate monohydrate and the Ca/P molar ratio was set to 1.67. The powders were screened through sieves having mesh sizes of 0.1, 0.3, 0.5, 0.7 and 1.0 mm to produce cement powders having particle sizes of 0.1 to 0.3 mm (powder 3), 0.3 to 0.5 mm (powders 4), 0.5 to 0.7 mm, 0.7 to 1.0 mm and 0.1 to 1.0 mm.

These cement powders were prepared in the same way as in Example 3-1 into calcium phosphate granular cements, which were then hardened. The resulting products were in the form of porous blocks having voids between granules.

The strengths of the hardened products produced using cement powders 3 and 4 were measured in the same way as in Example 3-1, and were found to be 21.0 kgf/cm$^2$ for powders 3 and 16.1 kgf/cm$^2$ for powders 4.

The hardening time of the product prepared using the powders 3 was measured, and found to be 10 minutes. Meanwhile, for measuring the hardening time, 60 parts by weight of physiological saline were mixed and kneaded with 100 parts by weight of the powders 3 to produce a cement paste, which was then charged into a mold frame having a diameter of 10 mm and a thickness of 3 mm. The cement paste with the outer mold frame was held in a constant temperature constant humidity vessel maintained at a temperature of 37° C. and a humidity of 100%, a round bar carrying a weight of 300 g was set on the surface of the cement paste, and the hardening time was found as the cumulative time which elapsed since kneading until no mark of the bar was formed on the cement paste surface.

Example 3-4

Powders were produced in the same way as in Preparation Examples 3-1 to 3-7 except that a mixture of calcium primary phosphate monohydrate and calcium secondary phosphate dihydrate at a molar ratio of 1:10 was used in place of calcium primary phosphate monohydrate and the Ca/P molar ratio was set to 1,594. The powders were screened through sieves having mesh sizes of 0.1, 0.3, 0.5, 0.7 and 1.0 mm to produce cement powders having particle sizes of 0.1 to 0.3 mm (powders 5), 0.3 to 0.5 mm, 0.5 to 0.7 mm, 0.7 to 1.0 mm and 0.1 to 1.0 mm.

These cement powders were prepared in the same way as in Example 3-1 into calcium phosphate granular cements, which were then hardened. The resulting products were in the form of porous blocks having voids between granules.

The hardening time of the hardened body prepared by using the powders 5 was measured in the same way as in Example 3-3 and was found to be seven minutes.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A calcium phosphate granular cement comprising mixed powders obtained by mixing α-type calcium tertiary phosphate with a calcium phosphate compound selected from the group consisting of calcium primary phosphate, calcium secondary phosphate and mixtures thereof at a Ca/P molar ratio of 1.35 to 1.49, a minimum diameter of each cement granule being 0.1 to 1.0 mm.

2. The calcium phosphate granular cement according to claim 1 wherein the calcium primary phosphate comprises calcium primary phosphate monohydrate.

3. The calcium phosphate granular cement according to claim 1 wherein the calcium secondary phosphate comprises a member selected from the group consisting of calcium secondary phosphate dihydrate, calcium secondary phosphate anhydride and mixtures thereof.

4. The calcium phosphate granular cement according to claim 1 wherein when a mixture of the calcium primary phosphate and the calcium secondary phosphate is used as the calcium phosphate compound, a mixing ratio of the calcium secondary phosphate is selected to be 10 wt % or less based on total weight of the powders.

5. The calcium phosphate granular cement according to claim 1 further comprising a water component selected from the group consisting of water and sterilized physiological saline, said water component being contained in an amount of 300 to 30 parts by weight to 100 total parts by weight of the powders.

6. A calcium phosphate granular cement comprising mixed powders obtained by mixing calcium quaternary phosphate with a calcium phosphate compound selected from the group consisting of calcium primary phosphate, calcium secondary phosphate and mixtures thereof at a Ca/P molar ratio of 1.30 to 1.90, a minimum diameter of each cement granule being 0.1 to 1.0 mm.

7. The calcium phosphate granular cement according to claim 6 wherein the calcium primary phosphate comprises calcium primary phosphate monohydrate.

8. The calcium phosphate granular cement according to claim 6 wherein said calcium secondary phosphate comprises a member selected from the group consisting of calcium secondary phosphate dihydrate, calcium secondary phosphate anhydride and mixtures thereof.

9. The calcium phosphate granular cement according to claim 6 further comprising a water component selected from the group consisting of water and sterilized physiological saline, said water component being contained in an amount of 300 to 30 parts by weight to 100 total parts by weight powders.

* * * * *